(12) United States Patent
Misener

(10) Patent No.: US 9,453,796 B2
(45) Date of Patent: Sep. 27, 2016

(54) METHOD FOR CALIBRATING CLINICAL CHEMISTRY INSTRUMENTS

(71) Applicant: Garland Christian Misener, Portland, ME (US)

(72) Inventor: Garland Christian Misener, Portland, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 14/583,385

(22) Filed: Dec. 26, 2014

(65) Prior Publication Data

US 2015/0112630 A1    Apr. 23, 2015

Related U.S. Application Data

(62) Division of application No. 12/798,290, filed on Apr. 1, 2010, now Pat. No. 8,949,059.

(60) Provisional application No. 61/211,580, filed on Apr. 1, 2009.

(51) Int. Cl.
    *G01N 21/55*    (2014.01)
    *G01N 21/27*    (2006.01)
    *G01N 21/59*    (2006.01)

(52) U.S. Cl.
    CPC ............ *G01N 21/55* (2013.01); *G01N 21/274* (2013.01); *G01N 21/59* (2013.01); *G01N 2201/062* (2013.01); *G01N 2201/12746* (2013.01)

(58) Field of Classification Search
    USPC ........................................................ 702/104
    See application file for complete search history.

(56) References Cited

U.S. PATENT DOCUMENTS

| 5,592,290 A | * | 1/1997 | Arai ...................... G01N 21/274 |
| | | | 356/243.5 |
| 7,616,317 B2 | | 11/2009 | Misener et al. .............. 356/446 |

FOREIGN PATENT DOCUMENTS

WO    WO/2008/140742    11/2008    ............. G01N 21/00

OTHER PUBLICATIONS

Carolyn F. Jones, Centroid wavelength of LEDs determined by broad-band measurement, SPIE vol. 3428, Jul. 1998, p. 130-140.*
Andrew Rabinovich, Framework for Parsing, Visualizing and Scoring Tissue Microarray Images, IEEE Transactions on Information Technology in Biomedicine, vol. 10, No. 2, Apr. 2006, p. 209-219.*
Fluorescence Spectroscopy, Principles of Fluorescence Spectroscopy, Lakowicz, J.R. 2006, Springer, p. 27-61.

* cited by examiner

*Primary Examiner* — Tung Lau
(74) *Attorney, Agent, or Firm* — Gerald T. Bodner

(57) ABSTRACT

A method of deriving correction for instrument-to-instrument variations in the illumination band centroid wavelengths and wavelength band shapes of the optical systems of clinical chemistry instruments includes the steps of determining the centroid wavelength and wavelength band shape of a light source used in the optical system of a clinical chemistry instrument to provide a determined wavelength band shape and centroid wavelength, comparing the determined wavelength band shape and centroid wavelength with a known reflection density or absorbance wavelength spectrum of a specific type of chemical reagent test to provide a correction value, and calculating the correction value, which is to be used to modify a reflection density or absorbance measurement taken by the instrument of a reagent test of the a specific type of chemical reagent test.

6 Claims, 5 Drawing Sheets

METHOD FOR CALIBRATING CLINICAL CHEMISTRY INSTRUMENTS

CROSS-REFERENCE TO RELATED APPLICATION

This application is a divisional of U.S. patent application Ser. No. 12/798,290, filed on Apr. 1, 2010, and entitled "Method for Calibrating Clinical Chemistry Instruments", which claims the benefit of priority under 35 U.S.C. 119 and/or 35 U.S.C. 120 to U.S. Provisional Application Ser. No. 61/211,580, filed on Apr. 1, 2009, and entitled "Method for Calibrating Clinical Chemistry Instruments", the disclosure of each of which is incorporated herein by reference in its entirety.

BACKGROUND OF THE INVENTION

1. Field of the Invention

The present invention generally relates to methods for calibrating clinical chemistry instruments.

2. Description of the Prior Art

Many clinical chemistry instruments measure optical changes caused by addition of a sample to test reagents. For example, some "dry chemistry" instruments measure reflectance factor changes after addition of a sample to a previously dry test slide. As a different example, some "wet chemistry" instruments measure transmittance changes after addition of a sample to a vessel, such as a cuvette, containing dissolved reagents. The sensitivity of either dry or wet chemistry instruments to measure optical changes in a sample-receiving reagent test slide or cuvette (or other sample container or liquid cell) may vary from instrument to instrument. Such instrument-to-instrument variations may result, among other things, from slight differences in the wavelength band shape or centroid of light emitted by a light source used in the optical system of the clinical instrument to illuminate the reagent test slide or cuvette.

Generally stated, to achieve consistency in optical measurements from instrument to instrument, calibration of each instrument is conventionally performed by running tests on the instrument with sample slides or cuvettes, comparing the measured test results with known reference or expected values, and adjusting the response of the instrument to compensate for the variability that may have arisen from, among other things, wavelength variabilities in the instruments' optical systems.

More specifically, control of the illumination band wavelength is important for accurate quantitation of dry chemistry test slides (or wet chemistry cuvettes). Wavelength control is substantially achieved by employing precision bandpass filters in the instruments' optical systems. However, even with precision control of the illumination or detection wavelength band, certain test assays, such as calcium, magnesium and albumin, may still require an offset to correct for differences in illumination wavelengths from instrument to instrument. For such chemistry slides or cuvettes, the reflection density or absorbance, respectively, bands are relatively narrow, where small deviations in the wavelength characteristics of the illuminating light could affect the sensitivity and accuracy of the instrument. Such assays (calcium, albumin and magnesium) are described in greater detail in the article, *Dry Chemistry: Analysis with Carrier—Bound Reagents*, authored by O. Sonntag, and published by Elsevier Science Publishers, Amsterdam, 1993, the disclosure of which is incorporated herein by reference. This problem of instrument-to-instrument variability in sensitivity is especially prevalent with test slides or cuvettes containing chromophores with a narrow reflection density or absorbance band or a steep baseline in the region of the band.

For example, in calcium dry reagent test slides, calcium ions complex with Arsenazo III, the reagent commonly used on such slides to quantify the calcium present in a blood, plasma, or serum sample under test, leading to a narrow absorbance band at approximately 680 nanometers. As can be seen from the graph shown in FIG. 4 depicting the reflectance spectrum of the Arsenazo III dye alone and after it is complexed with $Ca^{2+}$ (calcium ion), the Arsenazo III reagent itself is strongly absorbing in most of the visible spectrum, with absorbance dropping off steeply from about 660 nanometers to about 740 nanometers. The Calcium-Arsenazo III complex's band is quite narrow, that is, about 40 nanometers full (band) width at half (band) maximum (FWHM), as can be seen from the difference of reflectance factor spectra, shown in FIG. 5. Maximum instrument sensitivity to calcium will be achieved when the complex's reflectance factor difference band centroid and shape are well matched to the illuminating light's band centroid and shape. In this example, it is assumed that the response of the detector of the instrument's optical system is flat over the wavelength range encompassing the narrow absorbance band of the calcium complex. However, the detector's response may also contribute to the overall sensitivity of the instrument if the detector's response is not substantially flat over the illumination wavelength range.

If the wavelength band of the slide illuminating light generated by the light source is not centered on the calcium complex's absorbance band, the sensitivity of the instrument to absorbance changes will be lower than it would be if the complex's absorbance and source's emission bands were better matched. If identical test samples were run on substantially identical calcium test slides, but on instruments with varying sensitivity to the complex, then otherwise uncompensated instruments with lower sensitivity would generally report lower calcium concentrations than those with higher sensitivity to the complex.

Likewise, and more commonly, if identical samples were run on substantially identical calcium test slides, but on instruments with varying and uncompensated baseline reflection densities or absorbances, the instruments with lower baselines would generally report lower calcium concentrations than those with higher baselines. Thus, a "calcium offset" is added to some clinical chemistry instruments' measurements to compensate for differences in the measured Arsenazo III baseline resulting from the variation in the illumination wavelength from instrument to instrument. This offset, as stated previously, is necessary to compensate for the very steep baseline in the region of the Calcium-Arsenazo III complex's absorbance peak.

The worse the instrument-to-instrument control of the illumination band wavelengths and band shape, the more instrument-to-instrument variability in uncompensated calcium concentration measurements (and to a lesser degree, other chemistries) is expected.

Some clinical chemistry instruments employ light emitting diodes (LEDs) as the illuminating light source. Most LEDs are substantially wavelength stable (minimal or negligible drift over time) and exhibit a relatively long life. While for some LEDs, the emission band shape and centroid (or peak) wavelength characteristics are well controlled, this is not the general case. Unfortunately, for currently available LEDs, the centroid wavelength (and band shape) of light frequency emission vary from LED to LED, and the centroid cannot be held to such close tolerances, for example, 680 nanometers plus or minus one Angstrom, to avoid this problem. Conventionally, bandpass filters are used, as mentioned previously, to control the illumination light's wavelength. Generally, bandpass filter specifications are more accurate and precise than LED band shape and peak wavelength specifications.

However, bandpass filters add complexity and cost to the clinical chemistry instrument's structure and operation. Optical filters can deteriorate over a relatively short period of time due to humidity and aging. (Most filters are guaranteed by the manufacturer for only one year, although advances in rugged bandpass filter manufacture typically extend their useful lifetime to several years.) Therefore, it is not uncommon that a clinical chemistry instrument must be periodically serviced to replace the filters, which sometimes cannot be done by the user. Such, of course, requires more downtime of the instrument and increased costs to the user or the manufacturer.

Furthermore, the bandpass filters must be precisely positioned with respect to the light source. Conventionally, such filters are positioned with respect to the light source such that the plane in which the filter resides is perpendicular to the optical axis of peak intensity. However, as disclosed in co-pending application Ser. No. 11/286,079 filed on Nov. 23, 2005, and entitled "Reflectometer and Associated Light Source For Use In a Chemical Analyzer", the disclosure of which is incorporated herein by reference, it has been found that directing light from a light source, especially an LED, at an angle to the axis of peak intensity (that is, off-axis), to illuminate an object, such as a reagent test slide, creates a volume of homogeneous light which can solve problems associated with illumination homogeneity and Z-axis variability in the positioning of the object situated within that volume. But in this arrangement, the light from the LED sources is highly divergent and the illumination pathlengths are short. These angle-of-incidence and spatial constraints limit the effectiveness of using bandpass filters for the conditioning of the illumination band wavelengths.

Furthermore, calibrating each assembled clinical chemistry instrument by running performance tests using real reagent test slides is time consuming and presents difficulties. Instrument calibration using this conventional method may not be as precise as desired, since the offset adjustment of the instrument is at least partially based on performance tests using real test slides, making the results of this calibration also dependent on control sample preparation, stability, and handling, and also on the precision of the instrument measurements. Such variation may skew or increase the variability of the test results used in determining the offset to be applied to each instrument.

OBJECTS AND SUMMARY OF THE INVENTION

It is an object of the present invention to provide a method for calibrating a clinical chemistry instrument.

It is another object of the present invention to provide a method for compensating for wavelength variability of an object illuminating light source used in a clinical chemistry instrument.

It is still another object of the present invention to provide a method for calibrating a clinical chemistry instrument and adjusting for wavelength variability of unfiltered light emitting diodes forming part of an optical system used in the instrument.

It is a further object of the present invention to provide a method for determining an offset to be applied to a clinical chemistry instrument to compensate for wavelength variability of an object illuminating light source used in the instrument prior to incorporating the light source in the instrument.

It is still a further object of the present invention to provide a method for calibrating a clinical chemistry instrument which avoids the disadvantages of conventional calibration methods.

A method of the present invention is directed to calibrating an optical system of a clinical chemistry instrument. The optical system includes at least one light source and a light detector. The at least one light source may be a light emitting diode or a plurality of light emitting diodes simultaneously emitting light to illuminate an object. The at least one light source emits light to illuminate an object, such as a chemical regent test slide or cuvette. The illuminated object reflects or transmits light, and the light detector receives the light reflected or transmitted by the object that is illuminated by the light from the at least one light source. The light detector provides a signal in response to light received by the light detector.

The method of the present invention includes the steps of causing at least one light source to emit light, and measuring a wavelength band shape and centroid wavelength of the light emitted by the at least one light source for a predetermined wavelength range of light emitted by the at least one light source to provide a measured wavelength band shape and centroid wavelength. This measurement can be done prior to including one or both of the source and the detector within the clinical chemistry instrument. Then, the measured wavelength band shape and centroid wavelength are compared with a reference wavelength band shape and centroid wavelength. The reference wavelength band shape and centroid wavelength are used to define a reference response of the instrument to the reflection density or absorbance characteristics of the object (e.g., a reagent test slide or cuvette) to be illuminated by the at least one light source.

Then, in accordance with the method of the present invention, a correction is calculated. If an offset, this correction is added to a reflection density or absorbance value calculated by the instrument based on the signal provided by the light detector.

The correction may be in the form of a constant (or offset), a linear approximation or a higher order polynomial approximation, depending upon the complexity of the comparison of the measured wavelength band shape and centroid wavelength, the reference wavelength band shape and centroid wavelength, and the wavelength band shape and centroid wavelength of the object to be tested for the presence of the clinical chemistry analyte. The intensity of the wavelength band of the object to be tested is conventionally used to quantify the concentration of the clinical chemistry analyte. The correction adjusts the signal determined from wavelength band intensity of the object.

In a more preferred form of the present invention, a method of calibrating an optical system of a dry chemistry analyzer is described herein. The optical system includes at least one light emitting diode and a light detector. The at least one light emitting diode emits light having a wavelength band shape and a centroid wavelength to illuminate a chemical reagent test slide. The reagent test slide has a reflection density wavelength spectrum associated therewith which may be quantified by certain parameters, including a wavelength band shape and a centroid wavelength. The illuminated reagent test slide reflects light, and the light detector receives the light reflected by the reagent test slide that is illuminated by the light from the at least one light emitting diode. The light detector provides a signal in response to light received by the light detector.

The method of calibrating the optical system includes the steps of causing the at least one light emitting diode to emit light, and measuring the wavelength band shape and centroid wavelength of the light emitted by the at least one light emitting diode to provide a measured wavelength band shape and centroid wavelength.

The method further includes the step of comparing the measured wavelength band shape and centroid wavelength with the reference wavelength band shape and centroid wavelength to provide a correction.

The method of the present invention further includes the step of calculating a correction. The correction will be applied to a value of reflection density or absorbance calculated by the analyzer and based on the signal provided by the light detector.

In a slight modification to the method of the present invention described above, the at least one light emitting diode may include a plurality of light emitting diodes. The light emitting diodes have similar wavelength band shapes and centroid wavelengths and emit light simultaneously to illuminate the reagent test slide. If a plurality of light emitting diodes are used, then the measured wavelength band shape and centroid wavelength are based on the light simultaneously emitted by the plurality of light emitting diodes and are a composite of the wavelength band shapes and centroid wavelengths of the simultaneously energized light emitting diodes.

In yet another form, the present invention relates to a method of deriving a correction for instrument-to-instrument variations in the illumination band centroid wavelengths and wavelength band shapes of the optical systems of clinical chemistry instruments. This method includes the steps of determining the centroid wavelength and wavelength band shape of a light emitting diode or a plurality of light emitting diodes simultaneously energized, which are used in the optical system of a clinical chemistry instrument, to provide a determined wavelength band shape and centroid wavelength. Then, the determined wavelength band shape and centroid wavelength are compared with a known reflection density or absorbance wavelength spectrum of a specific type (e.g., calcium, magnesium, albumin and the like) of a chemical reagent test slide or sample cuvette having a wavelength band shape and centroid wavelength associated therewith to provide a correction.

The correction is to be applied to a reflection density or absorbance measurement taken by the instrument of a reagent test slide or sample cuvette of the specific type of chemical reagent test slide or cuvette.

As mentioned above, the specific type of chemical reagent test slide or cuvette may be a calcium test slide or cuvette having as a reagent such as Arsenazo III, a magnesium test slide or cuvette or an albumin test slide or cuvette, and so forth, each having chromogenic reagents usable for detecting the concentration of test samples. The correction which is applied to the reflection density or absorbance measurement may be in the form of a constant (or offset), a linear approximation, or a higher order polynomial approximation.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

In accordance with one form of the present invention, a method for calibrating a clinical chemistry instrument may be generally described as measuring the emission spectrum for previously calibrated (that is, intensity-balanced) light emitting diodes (LEDs) used in the optical system of the instrument, measuring the sensitivity spectrum, if such is necessary, of the reflection or transmission sensor (i.e., light detector) used in the optical system of the instrument, and using this information to set one or more corrections having an intercept value (offset), a slope value or higher-order terms, again if such are necessary, to compensate for instrument-to-instrument centroid wavelength and band shape characteristic variability. The emission wavelengths of the LEDs may be measured individually in order to determine if they meet acceptable criteria, or measurements may be taken of two or more LEDs of the same wavelength that are energized to simultaneously emit light. What is meant herein by the term "intensity-balanced" light emitting diodes is where the LEDs are calibrated to provide the same intensities. This intensity calibration method is described in detail in PCT Application No. PCT/US2008/005909, filed on May 7, 2008 and entitled "Chemical Analyzer", the disclosure of which is incorporated herein by reference.

Figure 1:
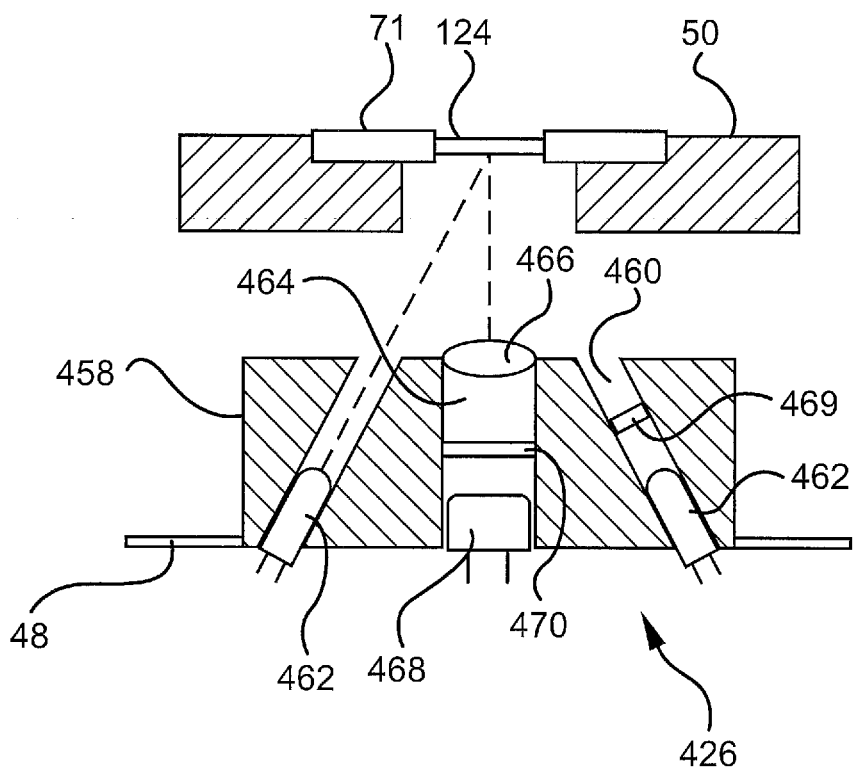
FIG. 1 is a side view of a class of reflectometers having one or more light emitting diodes and a light detector used in a clinical chemistry instrument.

More specifically, the method of the present invention calibrates an optical system of a clinical chemistry instrument. As shown in FIG. 1, the optical system, in its most basic form, includes at least one light source, such as a light emitting diode 462 or a plurality of light emitting diodes that have similar light emission characteristics (centroid wavelengths and wavelength band shapes, or peak intensities, for example) and a light detector 468. The at least one light source emits light to illuminate an object, such as a chemical reagent test slide 71 for dry chemistry analyzers or a sample cuvette containing a chemical reagent used in wet chemistry analyzers. The object, illuminated at certain wavelengths, reflects or transmits light, and the light detector 468 receives the light reflected or transmitted by the object illuminated by the light from the at least one light source. The light detector 468 provides a signal in response to the light received by the light detector to the electronic circuitry of the clinical chemistry instrument.

FIG. 1 shows the use of a bandpass filter 469 in the optical system, but such filters may be eliminated by the calibration method of the present invention. The remaining numbered components of the optical system shown in FIG. 1 are described in detail in the aforementioned co-pending patent application Ser. No. 11/286,079 and are not germane to the description of the invention presented herein.

In accordance with the method of the present invention, the at least one light source is energized to emit light. The wavelength band shape and centroid wavelength of the light emitted by the at least one light source is measured to provide a measured wavelength band shape and centroid wavelength. Then, the measured wavelength band shape and centroid wavelength are compared with a reference wavelength band shape and centroid wavelength to provide one or more correction values. The reference wavelength band shape and centroid wavelength are used to define a reference response of the instrument to the reflection density or absorbance characteristics of an object, such as a reagent test slide or cuvette, to be illuminated by the at least one light source. Certain reagents used on test slides or in sample cuvettes for detecting the presence of certain chemicals in a blood sample, such as calcium, magnesium, or albumin, and so forth, have known reflection density (or absorbance) spectra. The reflection density or absorbance spectral characteristics of the reagent test slides or cuvettes include band shape and centroid wavelength. As mentioned previously, for certain reagent test slides or sample cuvettes, such as those that are used for testing for the presence of calcium (e.g., Calcium-Arsenazo III slides) or magnesium, the wavelength band shape is relatively narrow. Therefore, if the centroid wavelength and wavelength band shape of the light source which is used to illuminate the reagent test slide or sample cuvette do not overlap in exactly the same way for each instrument, then the reflection density or absorbance measurements made by the instrument may differ from instrument to instrument depending upon how severe the differences are between the wavelength band shape and centroid wavelength of the instrument's illuminating light source from one instrument to another, and compared to the wavelength band shape and centroid wavelength of the reagent test slide or sample cuvette which is illuminated.

Then, according to the method of the present invention, a correction is calculated. The correction is applied to a value calculated by the instrument based on the reflected (or transmitted) light signal provided by the light detector.

The at least one light source may be a single light emitting diode, or may be a plurality of light emitting diodes. The plurality of light emitting diodes are energized to emit light simultaneously, and the measured band shape and centroid wavelength are based on the light simultaneously emitted by the plurality of light emitting diodes.

The emission bands of the light emitting diodes may be measured individually, by a simple algebraic procedure weighted equally and then summed to create a composite spectrum, or all of the light emitting diodes of a certain wavelength may be simultaneously energized to emit light, and the composite emission spectrum, including the band shape and centroid wavelength of the composite illumination, may be measured.

The illumination tests which are performed on the light emitting diodes of the optical system of the instrument can be performed before the instrument is even assembled, and that data is collected and follows the instrument through the assembly process. In other words, the light emitting diode tests can be performed "off-line." Neither a complete instrument nor a complete optical system is needed to perform the test, just the LED sources, their electronic drive circuitry and, if necessary, the light detector and its photoconversion circuitry.

Figure 2:
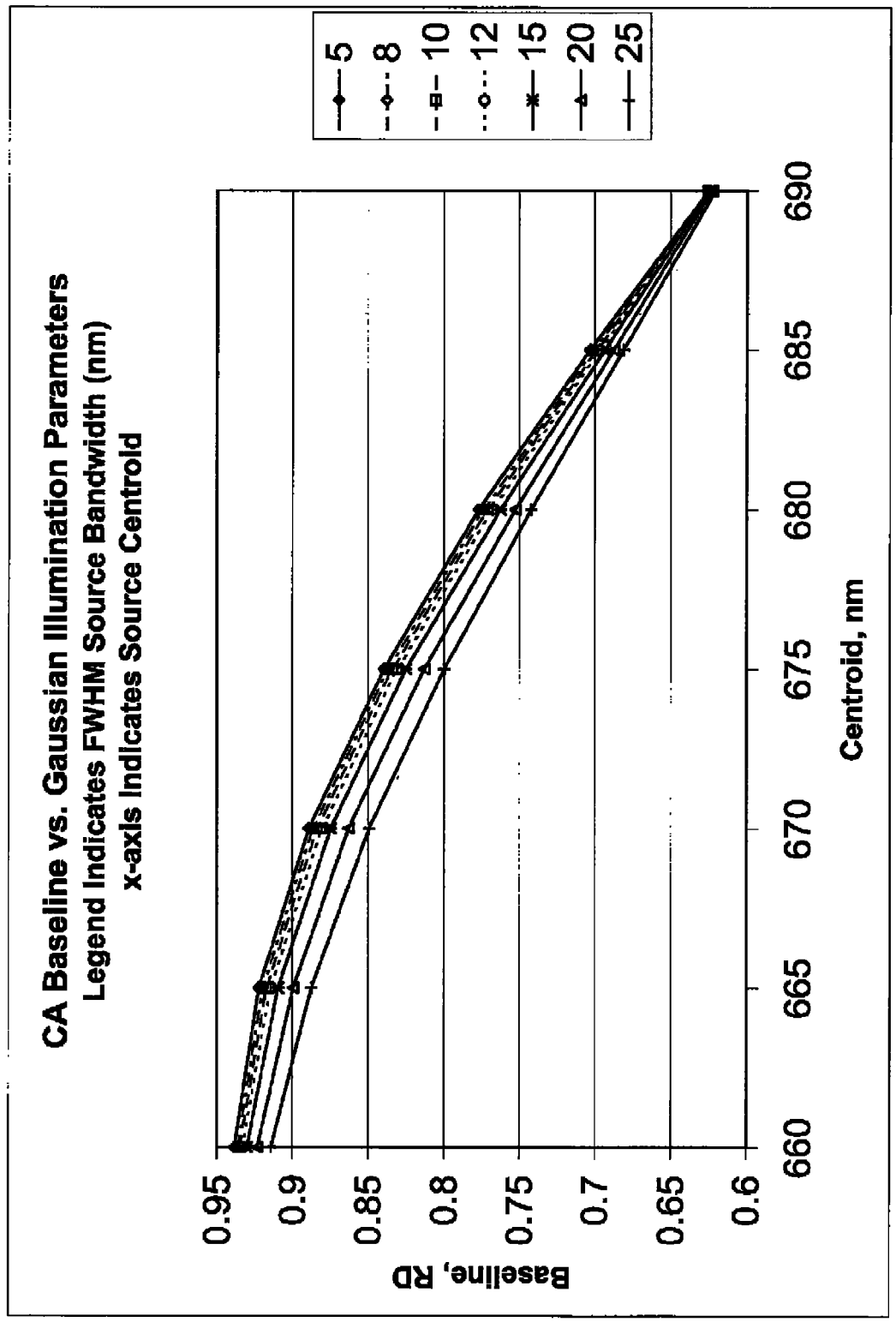
FIG. 2 is a graph of anticipated reflection density baselines for a calcium test slide (having Arsenazo III as the reagent) versus an illumination band modeled by a Gaussian band shape having the parameters of centroid wavelength and FWHM bandwidth of an illuminating light source of a clinical chemistry instrument, and illustrating the variations in the baselines for different illumination parameters.
Figure 3:
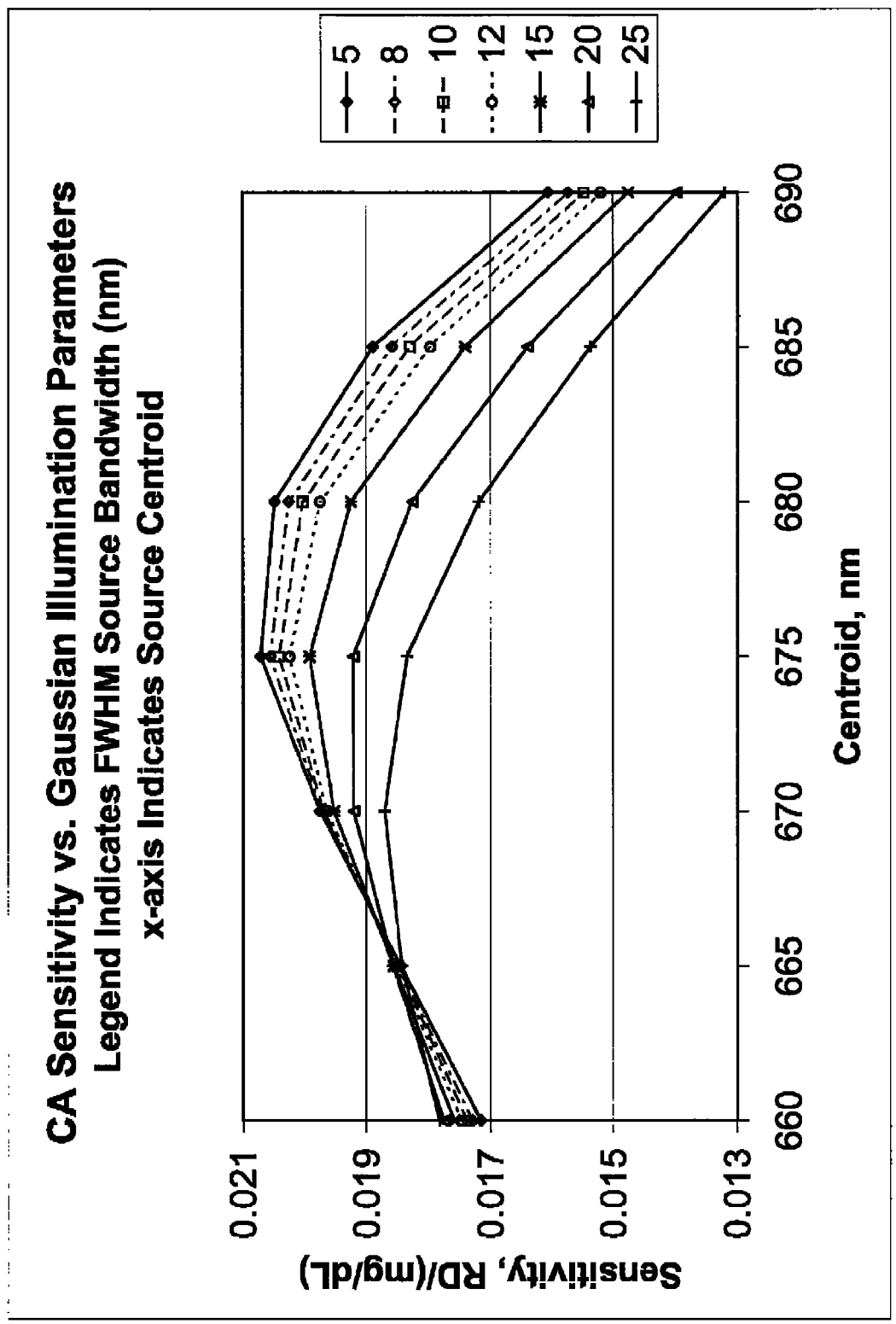
FIG. 3 is a graph of anticipated reflection density sensitivities to calcium concentration for a calcium test slide (having Arsenazo III as the reagent) versus an illumination band modeled by a Gaussian band shape having the parameters of centroid wavelength and FWHM bandwidth of an illuminating light source of a clinical chemistry instrument, and illustrating the variations in the instrument sensitivity to calcium concentration in milligrams per deciliter for different illumination parameters.
Figure 4:
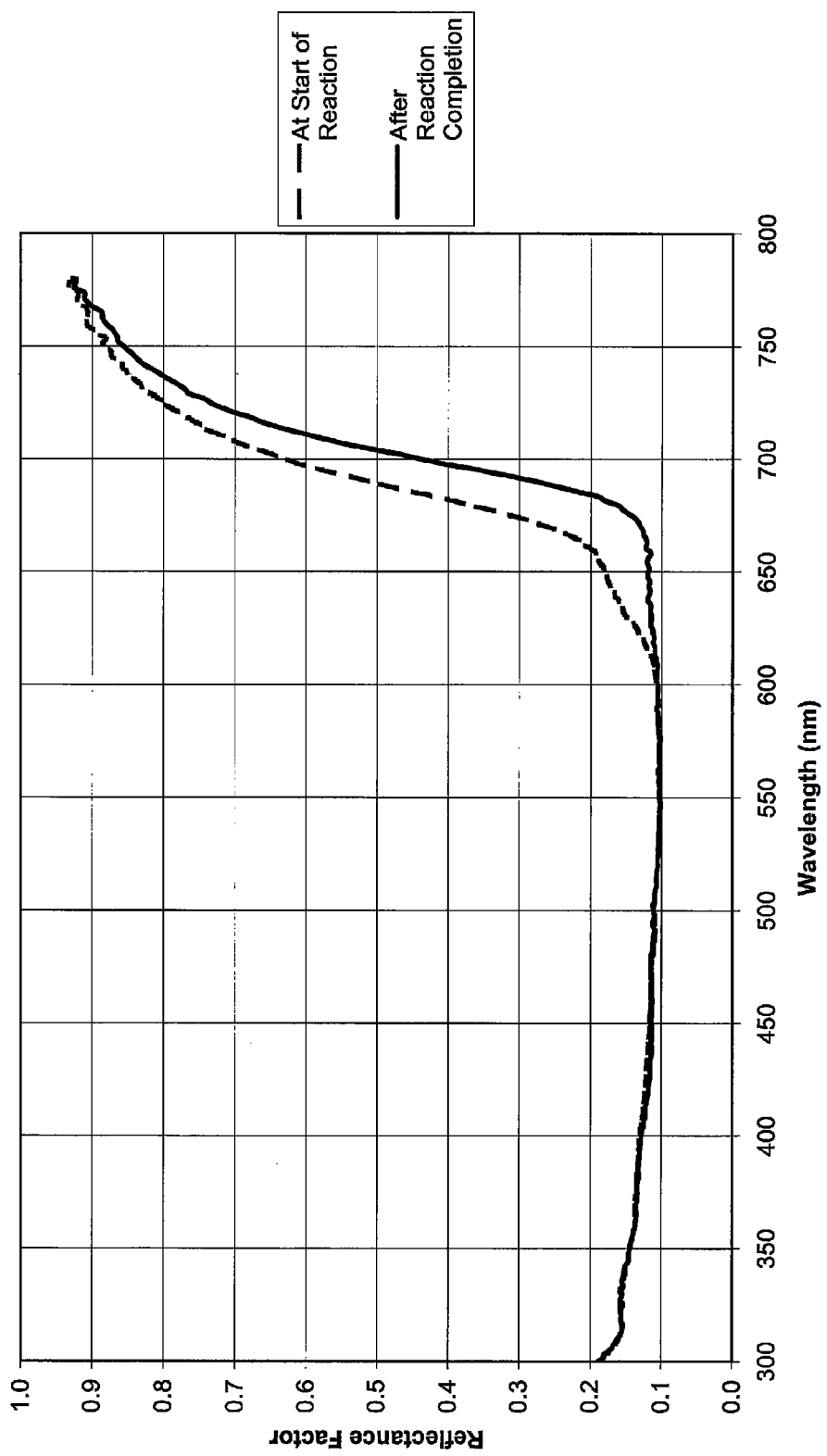
FIG. 4 is a graph depicting the reflectance factor spectra of the Arsenazo III reagent prior to and after it is complexed with $Ca^{2+}$ (calcium ion).

The following description, using the Calcium-Arsenazo III complex as an example, illustrates the applicability of the method of the present invention for calibrating for instrument-to-instrument wavelength and band shape characteristic variability. FIGS. 2 and 3 are charts which show that the calcium test slide baseline and sensitivity, respectively, follow regular patterns for simple wavelength parameters such as centroid wavelength and FWHM bandwidth. The information from which these charts shown in FIGS. 2 and 3 were derived include the reflection density spectra determined for the Calcium-Arsenazo III complex and the Arsenazo III background, and modeled Gaussian illumination bands of specified centroid (also peak, in this case) wavelength and FWHM bandwidth. What is meant by the Arsenazo III background is the reflection density spectrum that one gets from a calcium reagent test slide by a sample where no calcium is present. When calcium is present on the slide, then the Calcium-Arsenazo III complex, when compared to its baseline, will provide a peak in reflection density (or absorbance) at 680 nanometers.

In other words, in the example shown in FIGS. 2 and 3, illustrating the applicability of this method, the output of the light emitting diode is approximated by Gaussian-shaped bands, and it was determined how the overlap between the modeled light emitting diode bands and the Calcium-Arsenazo III complex reflection density spectrum changes as the illumination parameters (i.e., the centroid wavelength and FWHM bandwidth) change. From the two charts shown in FIGS. 2 and 3, it can be seen that the calcium baseline (intercept when $[Ca^{2+}]=0$ mg/dL) and slope (that is, sensitivity) follow regular patterns for the simple wavelength parameters of centroid wavelength and FWHM bandwidth.

The Y-axis in the chart of FIG. 2 represents the baseline (reflection density), and the X-axis represents the centroid wavelength of the Gaussian-modeled emissions of the light emitting diode for various FWHM bandwidths (measured in nanometers). Predictable differences in the calcium baseline and sensitivity can be observed when the centroid wavelength or FWHM bandwidth of the light emitting diode output vary.

For example, and as shown in the chart of FIG. 2, for an illumination wavelength centroid of 680 nanometers, having an FWHM bandwidth of 15 nanometers, it can be seen that the reflection density baseline (which would be the "b" constant in a linear approximation of the offset of $y=mx+b$) is equal to about 0.76. Now, in another instrument in which the illumination bandwidth has a centroid wavelength of 675 nanometers, with the same FWHM bandwidth (15 nanometers), the baseline on the Y-axis of the chart shown in FIG. 2 is about 0.82. The baseline has changed by 0.06 between the two instruments, the first having an illumination centroid wavelength at 680 nanometers, and the second having an illumination centroid wavelength at 675 nanometers. This is a rather significant change when measuring concentrations of a Calcium-Arsenazo III complex. Even more importantly, the calcium concentration derived from the reflection density measurements of this second instrument may be adjusted based on the predicted offset (which, in the chart shown in FIG. 2, can be the baseline difference) determined by measuring the illumination parameters of the light emitting diode of that particular instrument without the need for running tests on sample reagent test slides with the instrument in its assembled form. In the example given above, the 0.76 sensitivity intercept is set as the standard, and the 0.06 difference in the sensitivity intercept between the first instrument and the second instrument is used to determine the correction which must be applied to the reflection density calculated by the second instrument based on the measured reflection density of an actual calcium slide. In other words, if the second instrument were to be standardized to the first instrument's 0.76 sensitivity intercept, then 0.06 would be subtracted from a reflection density measured by the second instrument to correct its readings.

The chart shown in FIG. 3 plots the sensitivity of various instruments characterized by Gaussian approximated illumination parameters (i.e., centroid wavelength and FWHM bandwidth) and shows a sensitivity variation, that is, the slope (m) in a linear approximation of the correction, as stated in the equation y=mx+b, where m is the sensitivity (reflection density per calcium concentration stated in milligrams per deciliter), and the centroid wavelength of the instrument's illumination is set forth on the X-axis in nanometers, with several different illumination FWHM bandwidths plotted on the chart.

As can be seen from the charts of FIGS. 2 and 3, a correction may be provided which is a linear approximation having an intercept term and a slope term for more accuracy, if necessary, in determining a correction for the measured reflection density or absorbance from which the calcium concentration is determined by the instrument being calibrated. In a like manner, the correction may include higher order polynomial terms for even greater accuracy, although the usefulness of more than three terms is limited.

Although the examples shown in the charts of FIGS. 2 and 3 are based on a Gaussian model of the illumination, it should be understood that actual tests performed on the light emitting diodes, energized singularly or simultaneously, will be used to better advantage for calculating the correction required to calibrate each instrument to a desired standard.

The steps and logistics of a preferred form of the method of the present invention for implementing wavelength-specific compensation for clinical chemistry slides whose instrument-to-instrument reading accuracy would be significantly improved by use of this method will now be described. The term "optics module" is mentioned herein in connection with the description below of the preferred form of the calibration method of the present invention. The "optics module" refers to a sub-assembly of a clinical chemistry analyzer which includes a light source, such as one or more light emitting diodes (LEDs), a photosensor or detector, which receives light reflected from a reagent test slide, and electronic circuitry ("detection electronics"), including one or more memories and possibly a microprocessor for controlling the operation of the optics module.

Thus, in accordance with a preferred form of the calibration method of the present invention, the following steps, described in outline form, are performed:
1) Certain information is stored in a memory location of an optics module prior to running any clinical chemistry slide tests.
   a) In a test fixture, obtain intensity spectra of each LED=$I_{\lambda,w,j}$, and convert these to normalized spectra $S_{\lambda,w}$, one for each wavelength band.
   Subscript $\lambda$ indicates the wavelengths for which the intensity spectrum $I_{\lambda,w,j}$ is obtained. Wavelengths are typically expressed in nanometers (nm) and intensities are arbitrary values that are often the digitized photocurrent from the calibrated photosensor used to obtain the spectra. It is required that the spectrum $I_{\lambda,w,j}$ has been corrected for the baseline signals of the detection electronics, and that these have been calibrated for wavelength and sensitivity accuracy. The subscripts w and j indicate, respectively, the name of the wavelength band of the LED (for example, its centroid wavelength is nominally 650 nm) and the number of the specific LED in the wavelength band (for example, the second of three LEDs that the 650 nm band comprises).

A chemical analyzer may include, for example, three blue light emitting diodes (LEDs) which are energized simultaneously to illuminate a dry reagent chemical slide with light of a particular wavelength or range of wavelengths, perhaps three red LEDs energized simultaneously to emit light at a different particular wavelength or range of wavelengths from that of the blue LEDs, and perhaps three green LEDs, also energized simultaneously, to emit light at a third particular wavelength or range of wavelengths. Certain test slides are required to be illuminated by light of a particular wavelength or range of wavelengths; hence, the optics sub-assembly or module includes a plurality of red, green and blue LEDs.

According to this first step in the wavelength-compensation method, the spectrum for each red LED, green LED and blue LED is obtained using a spectrometer, for example.

i) Normalize each LED's intensity spectrum over the wavelength range of interest, as shown in Equation 1. Preferably, ignore (do not include) regions of the spectra outside of the wavelength range of interest that are indistinguishable from the baseline signals of the detection electronics or that are filtered out.

$$S_{\lambda,w,j} = \frac{I_{\lambda,w,j}}{\left(\sum_{\lambda=\lambda_{lower}}^{\lambda_{upper}} I_{\lambda,w,j}\right)} \qquad \text{(Equation 1)}$$

The wavelength range of interest is [$\lambda_{lower}$, $\lambda_{upper}$], and the wavelength range of the normalized spectrum $S_{\lambda,w,j}$ is therefore compressed to this range. In a preferred form of the invention, if the intensity spectrum data are collected at a consistent wavelength interval, then the summation in the denominator of Equation 1 can be applied to each measured intensity, as the summation implies. More generally, each intensity element $I_{\lambda,w,j}$ is multiplied by the defined extent (width) of the associated wavelength interval, $e_\lambda$; the summation then becomes $$\left(\sum_{\lambda=\lambda_{lower}}^{\lambda_{upper}} I_{\lambda,w,j} \cdot e_\lambda\right).$$

In this case, the area of normalized intensity spectrum becomes unity.

Equation 1 provides a normalized intensity spectrum $S_{\lambda,w,j}$ for each LED of a particular wavelength band (e.g., emitted by the red, green or blue LEDs). The wavelength range of interest is where the spectrum intersects the baseline (which is at zero). For a calcium test slide, the wavelength range of interest for red LEDs would be from about 630 nanometers to about 730 nanometers. To obtain a normalized intensity spectrum $S_{\lambda,w,j}$ for each LED of a particular band, one would divide the LED's intensity spectrum $I_{\lambda,w,j}$ by the sum of that LED's intensity spectrum $$\sum_{\lambda=\lambda_{lower}}^{\lambda_{upper}} I_{\lambda,w,j},$$

(preferably at a consistent wavelength interval) or the area of that LED's intensity spectrum $$\sum_{\lambda=\lambda_{lower}}^{\lambda_{upper}} I_{\lambda,w,j} \cdot e_\lambda$$

for a particular band and within the wavelength range of interest (for calcium, for example, $\lambda_{lower}$=630 nanometers and $\lambda_{upper}$=730 nanometers).

ii) Add all normalized spectra together and re-normalize, as shown in Equation 2.

$$S_{\lambda,w} = \frac{\sum_{j=1}^{n} S_{\lambda,w,j}}{n} \quad \text{(Equation 2)}$$

The number of LEDs in band w is n. The normalized spectra can be added without regard to the original intensity of the individual LED spectra because optics module calibration effectively equalizes the intensity contributions of each LED, as disclosed in PCT Application No. PCT/US2008/005909, the disclosure of which is incorporated herein by reference. These normalized spectra are stored in the optics module, one spectrum per wavelength band. It should be realized that, if the optics module has only one LED emitting light in a single wavelength band, then this step (Step 1) a) ii)) of adding the normalized spectra together and re-normalizing, as shown in Equation 2, may be omitted.

b) Also input to the optics module the normalized intensity spectrum of a reference LED set=$S_{\lambda,w_0}$. This is the normalized spectrum of a reference LED set for the wavelength, which may be generated artificially. Thus, this spectrum can be a Gaussian band with a known centroid wavelength and FWHM bandwidth, but it can equally well be a semi-arbitrary curve shape which better matches the band shapes for typical $S_{\lambda,w}$ cases. Although assignment of $S_{\lambda,w_0}$ is somewhat arbitrary, it should be near the center, and within the distribution, of expected $S_{\lambda,w}$ wavelength characteristics. This reference spectrum has the same wavelength range constraints of the $S_{\lambda,w}$ normalized spectrum, and should also be normalized.

c) Store the expected baseline reflectance factor for the chemistry of interest c (tested at wavelength band w) for the optics module with normalized LED spectrum. $S_{\lambda,w}$, as shown in Equation 3.

$$b_{w,c} = \sum_{\lambda=\lambda_{lower}}^{\lambda_{upper}} (r_{\lambda,c,b} \cdot S_{\lambda,w}) \quad \text{(Equation 3)}$$

Equation 3 applies for spectra intensities preferably obtained at consistent wavelength intervals and normalized by the sum method. If the spectra are normalized by the area method, then the summation in Equation 3 becomes $$\sum_{\lambda=\lambda_{lower}}^{\lambda_{upper}} (r_{\lambda,c,b} \cdot S_{\lambda,w} \cdot e_\lambda)$$

where the wavelength interval in this equation need not be the same as was used in the area normalization version of Equation 1 above, preferably if the wavelength interval used in normalization was very small. The standardized reflectance factor spectrum of the chemistry slide c run with a blank sample (similar to a real sample, but not containing the analyte) is $r_{\lambda,c,b}$. This spectrum should be obtained with a calibrated, baseline-corrected reflectance spectrometer, over a wavelength range that minimally includes the range $[\lambda_{lower}, \lambda_{upper}]$. Since $S_{\lambda,w}$ is normalized, $b_{w,c}$ is, like $r_{\lambda,c,b}$, in standardized reflectance factor units.

The chemistry of interest c could be calcium, magnesium, albumin and the like. The expected baseline reflectance factor is determined from a blank slide (having no analyte deposited thereon) for a particular chemistry (e.g., calcium, magnesium, etc.). The standardized reflectance factor spectrum associated with the test slides of a particular chemistry is measured once for each lot of slides, and is multiplied by the normalized spectra $S_{\lambda,w}$ of the light emitting devices for the particular wavelength band, and the multiplication result (i.e., the product) is summed over the same wavelength range of interest determined previously, that is, between $\lambda_{lower}$ and $\lambda_{upper}$ (630 nanometers to 730 nanometers for calcium), to determine the expected baseline reflectance factor for the optics sub-assembly or module undergoing wavelength compensation.

d) Store the reference baseline reflectance factor for the chemistry of interest c (tested at wavelength band w) for the reference optics module with normalized reference LED spectrum $S_{\lambda,w_0}$, as shown in Equation 4.

$$b_{w_0,c} = \sum_{\lambda=\lambda_{lower}}^{\lambda_{upper}} (r_{\lambda,c,b} \cdot S_{\lambda,w_0}) \quad \text{(Equation 4)}$$

The same standardized reflectance factor blank spectrum as in Section (c) above is used for $r_{\lambda,c,b}$. For the same reasons described in Section (c), Equation 4 becomes $$b_{w_0,c} = \sum_{\lambda=\lambda_{lower}}^{\lambda_{upper}} (r_{\lambda,c,b} \cdot S_{\lambda,w_0} \cdot e_\lambda)$$

in the area normalization case. Again, since $S_{\lambda,w_0}$ is normalized, $b_{w_0,c}$ is in standardized reflectance factor units.

This step is very similar to the preceding step, except that the reference spectrum of the reference LED is used as opposed to using the spectra of the optic module's LED wavelength band, in order to calculate this reference baseline reflectance factor for the reference LED, as opposed to the expected baseline reflectance factor for the optics module being wavelength-compensated, which expected baseline reflectance factor is module specific.

e) Store the chemistry-specific signal adjustment factor for an optics module with LED spectrum $S_{\lambda,w}$, and determine the ratio shown in Equation 5.

$$m_{w,c} = \frac{\sum_{\lambda=\lambda_{lower}}^{\lambda_{upper}} (r_{\lambda,c,d} \cdot S_{\lambda,w_0})}{\sum_{\lambda=\lambda_{lower}}^{\lambda_{upper}} (r_{\lambda,c,d} \cdot S_{\lambda,w})} \quad \text{(Equation 5)}$$

$r_{\lambda,c,d} = (r_{\lambda,c,s} - r_{\lambda,c,b})$ is a differential spectrum in standardized reflectance factor units—the difference between a sample spectrum $r_{\lambda,c,s}$ of the chemistry of interest (with the analyte present at an approximately normal range concentration) and the blank spectrum $r_{\lambda,c,b}$. Equation 5 becomes $$m_{w,c} = \frac{\sum_{\lambda=\lambda_{lower}}^{\lambda_{upper}} (r_{\lambda,c,d} \cdot S_{\lambda,w_0} \cdot e_\lambda)}{\sum_{\lambda=\lambda_{lower}}^{\lambda_{upper}} (r_{\lambda,c,d} \cdot S_{\lambda,w} \cdot e_\lambda)}$$

in the area normalization case.

$m_{w,c}$ is the ratio of the overlap of the differential spectrum with the reference LED source band to the overlap of the differential spectrum with the actual LED source band.

Figure 5:
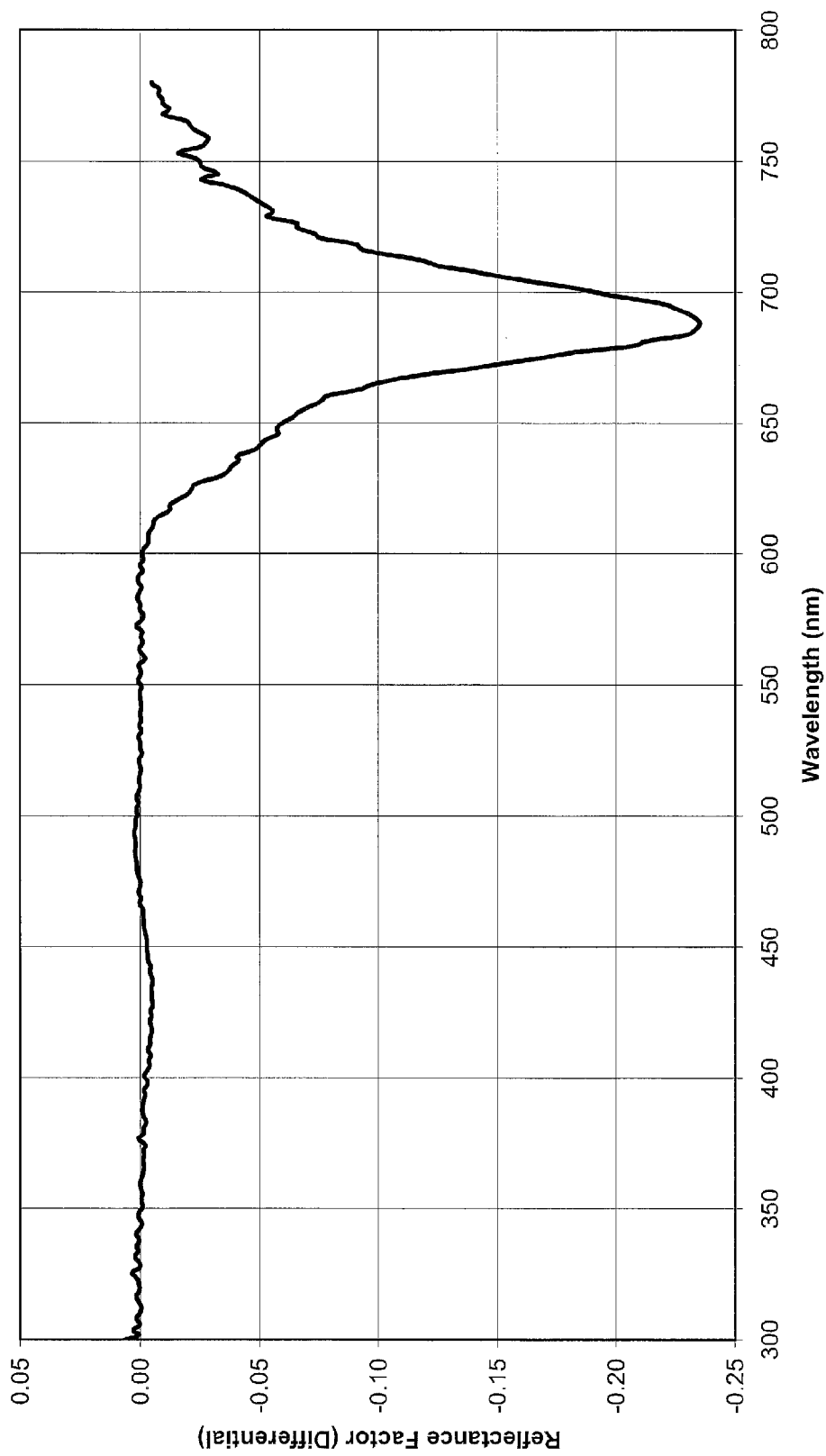
FIG. 5 is a graph depicting the difference of the two reflectance factor spectra shown in FIG. 4.

The differential spectrum (in reflectance factor units) is shown in FIG. 5. The signal adjustment factor, $m_{w,c}$, essentially, the slope term in a linear approximation correction. The slope term is expected to vary between about 0.5 and about 1.5. If the slope term is equal to one, then essentially the correction comprises the offset only.

2) Information to be determined after a clinical chemistry progress curve is obtained. The progress curve referred to herein is a set of reflectance factors versus time for a particular optics module of a chemical analyzer, and it is these reflectance factors which are corrected by using the expected baseline reflectance factors $b_{w,c}$ and $b_{w_0,c}$ and the chemistry-specific signal adjustment factor $m_{w,c}$ calculated previously using Equations 3, 4 and 5, respectively. In other words, this stage of the process is where a correction is made to the data obtained by the analyzer. To be clear, calculating the correction occurs in Step 1; applying the correction to the measured data occurs in Step 2.

Standardized reflectance factor (the output of a fully-calibrated optics module when a sample slide is measured) will be corrected as follows:

$$r_{w_0,c,s_0} = (r_{w,c,s} - b_{w,c}) m_{w,c} + b_{w_0,c} \quad \text{(Equation 6)}$$

$r_{w_0,c,s_0}$ = the corrected standardized reflectance factor of a sample s for chemistry c to be used for computing analyzer response (AR), corrected to the value expected for the normalized reference LED spectrum $S_{\lambda,w_0}$. Only one specific standardized sample reflectance factor $r_{w,c,s}$ must be converted for endpoint chemistries like CA (calcium), ALB (albumin), and MG (magnesium). To wavelength-compensate rate chemistries, the whole progress curve typically will be converted.

$r_{w,c,s}$ = the standardized reflectance factor for a given wavelength w measured by an optics module with normalized LED spectrum $S_{\lambda,w}$.

The reference baseline reflectance factor $b_{w_0,c}$, the expected baseline reflectance factor $b_{w,c}$ and the chemistry-specific signal adjustment factor $m_{w,c}$ have all been determined previously. Now, for this particular optics module, the standardized reflectance factor $r_{w,c,s}$ is determined. From Equation 6 and knowing the specific terms therein, the corrected standardized reflectance factor $r_{w_0,c,s_0}$ may be determined. The $w_o$ in $r_{w_0,c,s_0}$ means that the reflectance factor was compensated for wavelength, and the $s_o$ means that the reflectance factor is compensated to give the result one would expect with the standard spectrum $S_{\lambda,w_0}$.

Equation 6 is essentially the correction in a linear form applied to the actual measurements taken by the optics module of a chemical analyzer, the linear correction having a slope term (i.e., the signal adjustment factor $m_{w,c}$) and offset terms (i.e., the baseline reflectance factors $b_{w,c}$ and $b_{w_0,c}$). The corrected standardized reflectance factor for that particular optics module is used by the chemical analyzer in determining the concentrations.

Rearranging Equation (6) gives:

$$r_{w_0,c,s_0} = r_{w,c,s} m_{w,c} + (b_{w_0,c} - b_{w,c} m_{w,c}) \quad \text{(Equation 7)}$$

This simplifies to:

$$r_{w_0,c,s_0} \cong r_{w,c,s} + t_{w,c} \quad \text{(Equation 8)}$$

if the signal adjustment factor (i.e., the slope term) $m_{w,c} \cong 1$ and where $t_{w,c}$ is a new constant combining three terms from Equation 7. To the extent that the signal adjustment factor is unity, the correction becomes an offset only. More specifically, the constant $t_{w,c}$ is essentially the difference between the reference baseline reflectance factor $b_{w_0,c}$ the expected baseline reflectance factor b (when the signal adjustment factor $m_{w,c}$ is essentially equal to 1). This type of behavior is expected when the chemistry reflectance factor baseline (or intercept) varies considerably more than the specific, concentration-dependent reflectance factor slope over the wavelength region of interest.

However, it should be noted here that the narrow bandwidth of the calcium-Arsenazo III complex means that Equation 8 is not an accurate simplification of Equation 7.

3) Handling of $b_{w_0,c}$, $b_{w,c}$, and $m_{w,c}$.
   a) An off-line LED test fixture can be developed for obtaining the spectra (described in Sections ((1)a) and perhaps ((1)b) above), determining the $b_{w,c}$, $b_{w_0,c}$, and $m_{w,c}$, values for each wavelength-compensated chemistry, and storing the spectra and values in the optics module.
   b) The values are stored in each optics module's non-volatile memory.
   c) The values default to $b_{w_0,c}=b_{w,c}=1$ and $m_{w,c}=1$. This is equivalent to "do nothing" to compensate for wavelengths, and will be the case for most chemistries, since most will not be significantly wavelength-sensitive over the range of optics module LED wavelengths used for their illumination.
   d) When implemented, the LED test fixture obtains spectra and another fixture or system (with input of spectra described in Sections ((1)a) and ((1)b) above) determines the above values for each wavelength-compensated chemistry and stores the spectra and $b_{w,c}$, $b_{w_0,c}$ and $m_{w,c}$ in the optics module.

This preferred method is adaptable; a previously uncompensated or previously compensated chemistry can become the opposite with an upgrade of the $b_{w,c}$, $b_{w_0,c}$, and $m_{w,c}$ data stored in the optics module.

The method of the present invention provides a superior means of setting offsets and higher order scaling factors for all necessary chemistries used in clinical chemistry instruments, not just calcium alone. Thus, the wavelength-based analysis of the present method is not limited to simple centroid wavelengths and FWHM bandwidths and, as mentioned previously, does not rely on the Gaussian illumination band shape approximation, as actual measurements are performed on the light sources used in the instruments to determine the analyte concentrations.

As also mentioned previously, the sensitivity of the light detector used in the optical system of the clinical chemistry instrument may also be taken into account, if necessary. The spectral analysis of the light emitting diodes to be used in a particular instrument, as well as the wavelength-dependent radiant sensitivity of the detector to be used in the same instrument, may be measured and combined to provide a correction for reflection density or absorbance measurements made by the assembled instrument in operation.

Furthermore, the method of the present invention allows changing the instrument-specific offsets and sensitivities to account for changes in the performance of individual reagent test slide lots. For example, the Arsenazo III baseline may change from calcium slide lot to slide lot. For a given slide lot, the slide-to-slide readings are quite consistent. However, the calibration method of the present invention determines the offset to be applied to each instrument based on the Arsenazo III spectrum, and such may be variable from lot to lot. If this is the case and a new lot is provided to the clinician using the pre-calibrated instrument, software may be provided with the slide lot having the new spectrum information ($r_{\lambda,c,b}$ and $r_{\lambda,c,d}$) associated with that particular slide lot. The software may be downloaded into the instrument and, since the illumination parameters of the light emitting diodes used in that particular instrument are already known and programmed into the memory of the instrument, the correction may be recalculated by using the new spectra of the calcium slide lot. Conventionally, each slide lot includes software that tells the instrument that, for a particular slide lot, a certain calcium concentration corresponds to a measured reflection density. Therefore, it is quite easy to include with the software that accompanies the lot of reagent test slides information about the spectra of the slides of that particular lot.

The method of the present invention eliminates the inaccuracies of the time consuming calibration tests performed on assembled instruments using actual reagent test slides, which introduces other variables which may affect the accuracy of the calibration performed on the instrument. Furthermore, with the method of the present invention of deriving a correction for instrument-to-instrument illumination variability and applying the correction to the instrument, it is possible to eliminate the need for filters in the optical system of the instrument.

The terms "reflection density" and "absorbance" have been used herein in describing the method of the present invention for deriving a correction for instrument-to-instrument illumination wavelength variability. It should be understood that absorbance and reflection density are derived from the light transmittance (T) and reflectance factor (R), respectively, as follows:
   a. Absorbance=optical density=$-\log_{10}(T)$
   b. Reflection density=$-\log_{10}(R)$ where the range of both T and R are (0, 1], that is, greater than zero and less than or equal to one. Thus, absorbance is derived from measuring transmittance, and reflection density from measuring the reflectance factor. Reflection density is also known as "reflectance density" or "reflection factor density," where these latter terms are more specific. Reflection factor is more commonly measured in clinical chemistry instruments, where the measurement geometry permits detection of the reflected within a certain solid angle. Reflectance is specifically measured when reflected light is collected at all angles. The method described herein applies whether the reflectance factor or reflectance is measured, as long as the measurements made and corrections applied are for the same detection geometry.

Although the method of the present invention is described herein as being particularly useful for compensating for wavelength variations in LED (light emitting diode) emission bands, it should be understood that the invention is applicable for compensating for wavelength variations in the emission bands of other light sources, including but not limited to filtered white light sources, such as incandescent bulbs, arc lamps, flashlamps, and multi-line sources.

Furthermore, the calibration method described herein is extensible to compensating for wavelength variations in fluorescence detection systems. While more complicated, fluorescence wavelength compensation involves matching the wavelength characteristics of the excitation source with the excitation spectrum of the fluorophore, and the wavelength characteristics of the detection system with the emission spectrum of the fluorophore.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of calibrating an optical system of a dry chemistry analyzer, the method comprising the steps of:
   causing at least one light emitting diode of the optical system to emit light, the light emitted by the at least one light emitting diode of the optical system of the dry chemistry analyzer having a wavelength band shape and centroid wavelength, the at least one light emitting diode being provided to illuminate a chemical reagent test slide, the reagent test slide having a reflection density spectrum associated therewith, the reagent test slide, when illuminated by the at least one light emitting diode, reflecting light, the optical system of the dry chemistry analyzer having a light detector, the light detector receiving light reflected from the reagent test slide illuminated by the light from the at least one light emitting diode, the light detector providing a signal in response to the reflected light received by the light detector;

in an off-line test performed prior to the complete assembly of the dry chemistry analyzer, measuring the wavelength band shape and centroid wavelength of non-reflected light directly emitted by the at least one light emitting diode to provide a measured wavelength band shape and centroid wavelength;

comparing the measured wavelength band shape and centroid wavelength with a reference wavelength band shape and centroid wavelength; and calculating one or more correction values, the one or more correction values providing a correction which is used to modify the reflection density determined from the signal provided by the light detector.

2. A method as defined by claim 1, wherein the correction includes a constant.

3. A method as defined by claim 1, wherein the correction includes a linear approximation.

4. A method as defined by claim 1, wherein the correction includes a polynomial approximation.

5. A method as defined by claim 1, wherein the at least one light emitting diode includes a plurality of light emitting diodes, the plurality of light emitting diodes emitting light simultaneously, the measured wavelength band shape and centroid wavelength being based on the light simultaneously emitted by the plurality of light emitting diodes.

6. A method as defined by claim 1, wherein the specific type of chemical reagent test slide is at least one of a calcium test slide having as a reagent Arsenazo III, a magnesium test slide and an albumin test slide.

* * * * *